United States Patent [19]

Marschner

[11] Patent Number: 4,565,693

[45] Date of Patent: Jan. 21, 1986

[54] DEODORANT COMPOSITION

[75] Inventor: Frank W. Marschner, Whitehouse Station, N.J.

[73] Assignee: Colgate-Palmolive Company, New York, N.Y.

[21] Appl. No.: 319,527

[22] Filed: Nov. 9, 1981

[51] Int. Cl.$^4$ .......................... A61K 7/36; A61K 9/12
[52] U.S. Cl. ................. 424/67; 424/DIG. 5; 424/47
[58] Field of Search ..................... 424/67, 47, DIG. 5; 260/429.9

[56] References Cited

U.S. PATENT DOCUMENTS

| | | | |
|---|---|---|---|
| 2,236,387 | 3/1941 | Wallace, Jr. et al. | 424/67 X |
| 3,553,316 | 1/1971 | Rubino | 424/67 |
| 3,917,815 | 11/1975 | Kalopissis | 424/67 |
| 4,339,432 | 7/1982 | Ritchey et al. | 424/49 |

FOREIGN PATENT DOCUMENTS

| | | | |
|---|---|---|---|
| 0024176 | 2/1981 | European Pat. Off. | 424/67 |
| 197811 | 11/1978 | Fed. Rep. of Germany | 424/68 |
| 0061239 | 5/1977 | Japan | 424/68 |
| 1439403 | 5/1976 | United Kingdom | 424/319 |
| 701546 | 12/1983 | United Kingdom | 424/359 |

OTHER PUBLICATIONS

The Journ. of Soc. Cosm. Chemists, 1956, vol. 72, pp. 85 to 105, Klarman.
Dubsky et al., Chem. Abs., vol. 24, p. 4722, 1930.

*Primary Examiner*—Dale R. Ore
*Attorney, Agent, or Firm*—Herbert S. Sylvester; Murray M. Grill; Norman Blumenkopf

[57] ABSTRACT

Zinc glycinate as a non-irritating effective deodorant which chemically neutralizes odoriferous compounds and inhibits bacterial growth; deodorant compositions containing zinc glycinate as anhydrous or hydrated bis(glycino) - zinc salt; and methods of deodorizing the body by application to sweat areas.

The present invention relates to zinc glycinate as a deodorant active material having the dual function of chemically neutralizing body odors and inhibiting bacterial growth, particularly gram negative bacteria.

10 Claims, No Drawings

DEODORANT COMPOSITION

BACKGROUND AND PRIOR ART

The prior art is replete with antiperspirant compositions containing zinc salts per se or in combination with aluminum and/or zirconium salts, as the active antiperspirant agent. The Journal of the American Pharmaceutical Association, Vol. XLVII, No. 1, Jan. 1958, pages 25–31 discloses combination of zinc methionate and aluminum sulfamate, and zinc sulfate in combination with aluminum methionate. The Chemistry and Manufacture of Cosmetics by Maison G. de Navarre, 1941, page 261 lists the zinc salts in common use as antiperspirants to include the sulfate, chloride and sulfocarbolate; and further lists other zinc salts worth investigating which include benzoate, citrate, formate, glycerophosphate, perborate, salicylate, zinc-ammonium sulfate and zinc-potassium sulfate. U.S. Pat. No. 2,586,289 discloses zinc sulfamate as the antiperspirant in a cream base (oil-water emulsion); and U.S. Pat. No. 2,890,987 discloses zinc chloride in a stick form astringent. U.S. Pat. No. 3,325,367 discloses zinc sulfamate and zinc phenol sulfonate as antimicrobial astringent metal salts useful in antiperspirant creams, lotions, sticks and powders. U.S. Pat. No. 3,856,941 discloses astringent gels containing a mixture of aluminum salts with other metallic salts such as zinc salts including zinc chloride, zinc sulfate and zinc nitrate. U.S. Pat. No. 4,045,548 and U.S. Pat. No. 4,018,887 disclose dry powder antiperspirant agents including zinc sulfate, zinc sulfocarbolate and a zinc-aluminum complex in an aerosol antiperspirant composition. All of aforesaid zinc compounds function as antiperspirants which restrict the flow of perspiration as a means of combating unpleasant body odors.

The suppression of secretion of perspiration is known to have unfavorable effects on the skin, particularly skin irritation; and may also be corrosive to fabrics in contact therewith. This had lad to the use of anticorrosive agents in conjunction with antiperspirants as shown in U.S. Pat. No. 2,350,047, wherein a water insoluble metallic anticorrosive agent such as a zinc, magnesium or aluminum oxide, hydroxide or carbonate is added to an antiperspirant composition containing a water soluble astringent salt such as aluminum chloride or sulfate.

The prior art also discloses glycinates such as aluminum zirconium glycinate chelates as antiperspirant agents which restrict the flow of perspiration as noted in U.S. Pat. Nos. 4,049,792, No. 3,792,068 and No. 4,083,956 and British Patent No. 1,572,116. An amino acid, such as glycine, has been added to an antiperspirant composition as a discoloration inhibitor caused by the aluminum sulfamate antiperspirant, as shown in U.S. Pat. No. 2,586,288; and as a protective colloid to inhibit the corrosive action of astringent salts such as aluminum or zinc chloride or sulfate, as shown in U.S. Pat. No. 2,236,387.

Another method of combating body odors is the formulation of a deodorant composition containing a deodorant active agent which does not inhibit the flow of perspiration to any appreciable extent. U.S. Pat. No. 3,172,817 discloses a water soluble beta diketone zinc salt as an effective deodorant in sanitary napkins, diapers, insoles, creams, soaps, liquids, and body powders. U.S. Pat. No. 3,996,346 discloses a deodorant and antiperspirant composition containing zinc oxide and phenol which react in situ to form zinc phenate.

U.S. Pat. No. 4,172,123 discloses a deodorant composition containing a zinc salt of an unsaturated hydroxycarboxylic acid having 17 to 21 carbon atoms, such as zinc ricinoleate as the odor binding agent. The zinc ricinoleate is described as having odor-binding and fungistatic activity.

European Application No. 0-024-176 by Unilever discloses deodorant compositions comprising a suspension of zinc carbonate as the deodorant active material, which reduces axillary body odor without suppressing the secretion of perspiration.

U. K. Patent Application G. B. 2,052,978 A discloses a zinc-glycine combination in solution at a pH of 4.5–8.0 as an anticalculus-antiplaque agent in an oral composition. The zinc salt may be added to the mouthwash as zinc glycinate directly or the zinc salt and the glycine may be added separately. The zinc ions are kept in solution a pH 4.5–8 by using glycine.

However, there is no disclosure of zinc glycinate as a deodorant active material possessing the dual function of inhibiting bacterial growth and chemically neutralizing body odors.

SUMMARY OF THE INVENTION

The primary object of the invention is to provide a novel non-irritating, highly effective deodorant compound which neutralizes unpleasant odors through chemical interaction and also inhibits bacterial growth.

Another object of this invention is to provide deodorant compositions which are substantially non-irritating to the body, containing a zinc glycinate compound as the essential antibacterial active agent.

Still another object of this invention is to provide a deodorant composition containing anhydrous or hydrated zinc glycinate as the essential deodorant agent.

Still another object of the invention is to provide deodorant compositions containing zinc glycinate, which may be in the form of a liquid, cream, gel, solid stick, powder or spray.

Another object of this invention is to provide a process for deodorizing odorous body locations by contacting with a deodorizing amount of a compound which is a zinc glycinate in anhydrous or hydrated form.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects and in accordance with the present invention, as embodied and broadly described herein, the deodorant product of this invention comprises a deodorizing amount of zinc glycinate in a non-toxic cosmetically or dermatologically acceptable vehicle. The vehicle may be a powder such as talcum powder or foot powder; a lotion such as a roll-on composition; a cream base (oil-water emulsion); a gel such as a deodorant stick; or an aerosol or non-aerosol spray.

More specifically, present invention relates to zinc glycinate as a novel deodorant agent which chemically neutralizes body odors and inhibits bacterial growth, suspended or dissolved in a cosmetically acceptable vehicle; and to a process of deodorizing the human body by contacting said odoriferous locations with said zinc glycinate-containing deodorant compositions.

Zinc glycinate was reported synthesized by J. V. Dubsky and A. Rabas in Chem. Abstracts Vol. 24, 4722 (1931), by boiling glycine with a zinc oxide solution. The reaction product is described as a zinc metal amino acid complex which exists as the bis (glycino) — zinc (11) monohydrate $(NH_2CH_2COO)_2Zn \cdot H_2O$.

It has been found that the anhydrous zinc glycinate can be obtained by precipitating zinc glycinate from an alcoholic solution and using an excess amount of the glycine reactant to lower the solution pH and permit all the zinc oxide to react. More specifically, glycine and zinc oxide are added to water and the mixture is heated to 93° C. and mixed until a clear solution is obtained. Absolute ethanol is then admixed therewith, which precipitates out zinc glycinate, leaving residual glycine in solution. The soft, white, nonhygroscopic crystals are filtered, washed with absolute ethanol, and dried in a vacuum oven or air dried. Analyses of the compound showed it to contain zinc and glycine ratios typical of anhydrous zinc glycinate. Its infrared spectrum resembled that of nickel glycinate. The reaction proceeds according to the following equation:

$$ZnO + 2(NH_2CH_2COOH) \rightarrow (NH_2CH_2COO)_2Zn + H_2O \quad (1)$$

| ANALYSES | % | ANALYZED RATIO | THEORETICAL RATIO |
|---|---|---|---|
| Zinc | 31.7 | 32.45 | 30.62 |
| Glycine | 66.0 | 67.55 | 69.38 |
| Water | 2.5 | | |

The zinc glycinate is an odorless, low density, white, non-hygroscopic crystalline material, insoluble in ethanol and slightly soluble in water, a solubility of about 6 grams per 100 ml cold water. The pH of a 1% aqueous solution of zinc glycinate is about 8.0 (within the range of 7.9 to 8.7).

It has also been found that zinc glycinate can be prepared by reacting a zinc halide, and as the chloride, with glycine according to the following equation:

$$ZnCl_2 + 2(HOOC-CH_2NH_2) + 2NaOH \longrightarrow Zn(OOC-CH_2NH_2)_2 + 2NaCl + 2H_2O \quad (2)$$

In this method, zinc chloride and glycine are also reacted at elevated temperatures in an aqueous medium until a clear solution is obtained, but the zinc glycinate is precipitated by the addition of sodium hydroxide.

Still another method of producing zinc glycinate has been found, which utilizes the reactants zinc carbonate and glycine, as illustrated by the following equation:

$$ZnCO_3 + 2(HOOC-CH_2NH_2) \rightarrow Zn(OOC-CH_2NH_2)_2 + CO_2 + H_2O. \quad (3)$$

In this method, the zinc carbonate is added to an aqueous solution of glycine. The $CO_2$ is liberated and the solution is evaporated to dryness or spray dried to obtain white crystals of zinc glycinate. This method does not require the addition of a precipitating agent such as ethanol or sodium hydroxide as in the first two methods explained above, rendering it a more commercially viable method (less costly and more direct).

It has been found that zinc glycinate and deodorant products containing zinc glycinate are highly effective, both for odor prevention as well as for neutralizing existing body odors such as underarm odors, foot odors and the like. In vitro deodorant tests showed that a solution of synthetic sweat odor was completely deodorized by zinc glycinate. In vivo deodorant tests having 1% aqueous solution of zinc glycinate swabs on armpits with moderate to heavy odor resulted in complete deodorization of the armpits. Deodorant compositions containing zinc glycinate, such as unperfumed roll-on products containing 10% zinc glycinate in suspension, also showed instantaneous deodorizing of existing odors as well as the prevention of odor formation for periods as long as 48 hours.

The deodorant mechanism of zinc glycinate is similar to that of sodium bicarbonate, namely the neutralization of odors through acid/base chemical interaction. However, sodium bicarbonate hydrolyzes to form sodium hydroxide (NaOH), whereas zinc glycinate forms zinc hyroxide $Zn(OH)_2$, which is a milder base with lower potential skin sensitivity. The deodorant capacity of zinc glycinate (the weight required to chemically neturalize the odor of x ml of synthetic sweat solution) is about the same as sodium bicarbonate. Zinc glycinate solutions, however, are pH stable, whereas sodium bicarbonate solutions are not, since they release $CO_2$ and gradually form sodium carbonate, a known skin irritant.

It has additionally been found that zinc glycinate also provides superior antibacterial properties compared to sodium bicarbonate. Using the Halo test and measuring the Zone of Inhibition in mm, using $150 \times 25$ mm plastic plates and 12.7 mm disks, the following comparative results were obtained.

TABLE 2

| Organism | 5% Aqueous Sodium Bicarbonate | 5% Aqueous Zinc Glycinate |
|---|---|---|
| Staph. aureus | 0 | partial inhibition |
| E. Coli | 0 | 19.5 mm |
| P. Aeruginosa 10145 | 0 | partial inbibition |

Zinc glycinate is effective in aqueous solutions, in suspensions of various types and in powder form. Although zinc glycinate is not an antiperspirant, it can be incorporated into practically all antiperspirant type formulations by those familiar with the art. Various deodorant forms include aqueous solutions, alcoholic or cyclomethicone suspensions, pastes, creams, aerosol or non-aerosol sprays and solid sticks which incorporate volatile or non-volatile polar or non-polar vehicles.

Polar non-volatile vehicles may include polyhydric alcohols such as glycerine, propylene glycol, butylene glycol or polyglycols or ethoxylated glycols thereof, or polyethylene glycol.

Non-polar non-volatile vehicles may include small emollient oils such as isopropyl myristate, isopropyl palmitate, octyl palmitate, fatty alcohols, fatty amides, ethoxylated or propoxylated fatty alcohols or acids, fatty glycerides or silicone.

Polar volatile vehicles may include water, monohydric alcohols such as ethanol, isopropanol or methanol.

Non-polar volatile vehicles may include hydrocarbons, fluorinated hydrocarbons, and cyclomethicones or mixtures thereof.

Another suitable base for zinc glycinate is talc, starch, modified starches, oat powder, or other mineral or grain derived powders with particle sizes ranging between 5 and 100 microns which impart a smooth non-gritty feel on the skin.

Deodorant compositions in accordance with this invention will usually comprise about 1 to 20% zinc glycinate in solution or suspension form and may contain upwards of 50% in powder type products.

Certain ingredients to be avoided in zinc glycinate formulations which deactivate its deodorant properties include inorganic or organic acids. Also water soluble metal salts of fatty acids such as sodium stearate will generally react with zinc glycinate in the presence of water to form insoluble zinc stearate.

More specifically, the non-toxic cosmetically or dermatologically acceptable vehicle may be in the form of a lotion which comprises a liquid carrier such as a volatile lower alcohol or an aqueous alcoholic media, preferably ethanol containing a lesser amount of water, having particular utility in a roll-on composition. Usually the liquid carrier also comprises a suspending or thickening agent such as fumed silica, hydroxyethyl cullulose and other cellulose derivatives, hydrophobic clays, and combinations thereof, to maintain the zinc glycinate deodorant powder in suspension. Non-volatile polar or non-polar ingredients may be added to effect the deposition of a dray, non-sticky invisible film on the skin upon evaporation. Said non-volatile agents include polyhydric alcohols such as glycerine, propylene glycol and butylene glycol and polyglycols thereof, and emollient oils such as wheat germ oil, and any other alcohol soluble oils including isopropyl myristate, isopropyl palmitate, other fatty esters, fatty amides, fatty alcohols, fatty ethers such as stearyl ether, ethoxylated fatty alcohols or acids. The amount of emollient present is minor, about 1–5%. Roll-on compositions (dispensed from a roll-on container) in accordance with this invention will usually comprise about 10–20% deodorant active powder, about 0.1–2% suspending agent, about 10–30% nonvolatile polar ingredients such as polyhydric alcohols, in a liquid carrier containing about 55–75% monohydric alcohol and 5–25% water.

The vehicle may also be in the form of a cream which usually comprises an emulsion of a fatty material in water. Fatty materials may include fatty esters, cetyl alcohol, ethoxylated fatty alcohols, fatty glycerides, and emollients as listed above. The water content of the cream may constitute about 25–70% of the cream base and with a deodorant active agent content of about 5–15%.

The cream may also be an anhydrous cream comprising a volatile silicone vehicle such as cyclomethicone containing emollients, suspending agents, thickening agents and other suitable ingredients to produce a product of desired consistency.

The zinc glycinate deodorant powder of this invention may also be suspended in a stick base vehicle which usually comprises a monohydric or polyhydric alcohol or combination thereof gelled with a fatty alcohol or fatty amide. This base may also contain emollients, suspending agents and other non-volatile polar and non-polar ingredients as set forth in the aforedefined roll-on formulations.

The zinc glycinate deodorant powder may also be suspended in a liquid vehicle comprising the carrier liquid and a liquified gaseous propellant to formulate an aerosol spray. Additional conventional ingredients as described above may be added, to effect a suitable deodorant spray product.

The vehicle may also be an oil base as in an ointment formulation, wherein the zinc glycinate is intimately admixed with the oil and fatty acid esters.

Another suitable base for the zinc glycinate deodorant is talc as in a talcum powder product.

The amount of the powdered zinc glycinate deodorant present in the deodorant compositions may vary over a wide range and may be as high as 50% by weight, as in ointment or talcum powders. However, about 1–20% is the preferred range in most cosmetic compositions.

DETAILED DESCRIPTION OF THE INVENTION

The following specific examples are further illustrative of the present invention, but it is understood that the invention is not limited thereto. All amounts of various ingredients are by weight unless otherwise specified.

Preparation of Zinc Glycinate

EXAMPLE 1

| Components | Amount |
|---|---|
| $ZnCl_2$ | 13.6 gm. |
| Distilled water | 62.9 gm. |
| Glycine | 7.5 gm. |
| NaOH (50% solu.) | 16.0 gm. |

13.6 gms. of $ZnCl_2$ (1 mole) is dissolved in 62.9 gms. hot distilled water and 7.5 gms. of glycine (1 mole) is added to the $ZnCl_2$ solution. A clear solution is obtained. NaOH is added, resulting in the formation of a precipitate which is filtered out of solution, washed with ethanol, and air dried overnight. The precipitate crystals have a pH of 8.0, that of zinc glycinate.

The zinc glycinate crystals are added to a synthetic sweat solution containing the odorous fatty acid components of human sweat, such as acetic acid, isovaleric acid, etc. The addition of the zinc glycinate causes the pH of the fatty acid solution to rise to 7.0 and the solution is completely deodorized. Zinc glycinate deodorizes within the pH of 8 and 7.

EXAMPLE 2

| Components | Amount (gms.) |
|---|---|
| $ZnCl_2$ | 13.6 (1 mole) |
| Glycine | 15.0 (2 moles) |
| 50.5% NaOH solu. | 15.8 |
| Distilled Water | 55.5 |

The same procedure is followed in preparing zinc glycinate crystals as in Example 1. One gram of zinc glycinate dissolved in distilled water deodorizes 15 ml of titrated fatty acid solution from pH 8.0 to 7.0, below which a mild odor appears. Prior thereto, no odor is evident showing complete deodorization by zinc glycinate.

The addition of 1 gm glycine to 1 gm zinc glycinate in distilled water reduces the solution pH from 8.6 to 7.3. This combination is not as effective as zinc glycinate alone. The mixture deodorizes only 5 ml of fatty acid sweat solution. However, odor reduction is achieved from pH 7.3 to pH 6.5, below which some odor is present. Thus, no deodorizing properties can be attributed to glycine. As a matter of fact, the presence of free glycine reduces the deodorizing capacity of zinc glycinate.

EXAMPLE 3

| Components | Amount (gms.) |
| --- | --- |
| Glycine | 52.5 |
| Zinc Oxide | 20.35 |
| Distilled Water | 300.0 |

The above mixture is heated to 200° F. until a clear solution is obtained. 300 gms absolute ethanol is added with mixing and a precipitate is formed. The mixture is filtered using #1 Whatman filter paper, and the crystals are washed several times with absolute ethanol. The white crystalline, non-hygroscopic precipitate is placed in a drying pan and air dried at 120° F. overnight. The pH of a 1% aqueous solution is 8.3. The pH of a 7% saturated aqueous solution is 8.0. The zinc glycinate has a water solubility of about 6 gm/100 cc water.

A small quantity of a 1% aqueous zinc glycinate is addded to synthetic sweat odor solution resulting in complete deodorization

EXAMPLE 4

| Components | Amount (gms.) |
| --- | --- |
| Glycine | 15 |
| Zinc Carbonate | 12.5 |
| Distilled Water | 90 |

The glycine is dissolved in water and the zinc carbonate is added. $CO_2$ is liberated and the solution is evaporated to dryness to obtain white crystals of zinc glycinate which may be the monohydrate form of zinc glycinate. A 1% aqueous solution has a pH of 7.9. In lieu of evaporation, the solution may be spray dried to obtain the zinc glycinate crystals.

A 5% aqueous solution of the product, deodorizes a solution of artificial sweat.

Deodorant Compositions

EXAMPLE 5

Roll-on Deodorant

| Ingredient | % |
| --- | --- |
| Part 1 | |
| Deionized Water | 15.0 |
| Propylene Glycol | 10.0 |
| Hydroxyethyl cellulose | 0.4 |
| Part 2 | |
| SD 40 Ethanol | 61.6 |
| Zinc Glycinate | 10.0 |
| Fumed Silica | 0.5 |
| Part 3 | |
| Wheat Germ Glyceride | 1.0 |
| Polyoxypropylene Stearylether | 1.5 |

Part 1 ingredients are mixed, and preferably heated to 140° F., until a thick, uniform dispersion is formed. Part 2 ingredients are homogenized and added to the thick uniform mixture of Par 1 with mixing. Part 3 ingredients are admixed into the Part 1 and 2 mixture and preferably homogenized. A thick, stringy pituitous mixture is obtained which is placed in a conventional roll-on container.

This product is tested by adding 1 g of this roll-on product to 50 ml of a 5% aqueous synthetic human sweat solution. Total effective deodorizing is achieved in-vitro.

In-vivo testing consists in applying this product only to the right armpit, leaving the left armpit as a control. Underarm odor is rated after 24 and 48 hours.

| Time | Control Arm | Test Arm |
| --- | --- | --- |
| 24 hrs. | slight odor | no odor |
| 48 hrs. | moderate to heavy odor | no significant odor |

Another in-vivo test consists in washing underarms but applying nothing in order to generate moderate odor under both armpits for about 24 hours. This roll-on product is applied to one armpit with almost instant deodorizing action. This product is applied to the second armpit with similar results.

The zinc glycinate product exhibits both odor prevention properties as well as neutralizes existing underarm odors.

No irritation is observed with the product on any occasions.

Aerosol Deodorants

| | Example 6 | Example 7 |
| --- | --- | --- |
| Part 1 | | |
| Isopropyl Palmitate | 1.44 | 2.88 |
| Bentone 38[1] | 0.20 | 0.40 |
| Propylene Carbonate | 0.06 | 0.12 |
| Part 2 | | |
| Cyclomethicone | — | 4.0 |
| SD 40 Alcohol | 5.0 | — |
| Zinc Glycinate Powder | 2.0 | 2.0 |
| Perfume | 0.1 | 0.1 |
| Part 3 | | |
| Isobutene | 91.2 | 90.5 |
| | 100.0 | 100.0 |

[1] Quaternium 18 Hectorite

Procedure:

Part 1 ingredients are combined and homogenized under high shear conditions to form a gel.

Part 1 gel is added and mixed with SD 40 alcohol or cyclomethicone, and zinc glycinate under and perfume are admixed. The slurry is placed in an aerosol container, crimped, and gassed with isobutane.

Both product sprays produce an invisible film on the skin, which affords almost instant deodorization.

EXAMPLE 8

Anhydrous Deodorant Cream

| Ingredients | % |
| --- | --- |
| Part 1 | |
| Cyclomethicone | 51.0 |
| Isopropyl myristate | 3.3882 |
| Bentone 38 | 0.4706 |
| Propylene carbonate | 0.1412 |
| Stearamide MEA (monoethanolamide) | 1.5 |
| Zinc stearate | 1.5 |
| Polyoxyethylene (20) isohexadecyl ether | 2.0 |
| Cocomonoethanolamide | 3.0 |
| Part 2 | |
| Zinc glycinate powder | 10.0 |
| Part 3 | |
| Dryflo starch (aluminum starch octenyl succinate) | 25.0 |
| Part 4 | |

| -continued | |
|---|---|
| Ingredients | % |
| Colloidal silica | 2.0 |

Part 1 ingredients are mixed and heated to 225° F. to form a translucent solution. The mixture is cooled to 180° F.

The zinc glycinate powder is admixed with Part 1 and the temperature is maintained at 150° F.

The starch is admixed with Parts 1 and 2 and the temperature is maintained at 150° F.

The colloidal silica is admixed with combined Parts 1, 2 and 3 while maintaining the temperature at 150° F.

The final mixture is poured into containers and allowed to cool. The mixture thickens, as it cools to 100° F., into a non-pourable soft cream consistency.

The addition of this cream to a synthetic sweat solution effects complete deodorization almost instantaneously.

Known equivalents may be substituted for the specific ingredients in above compositions.

The zinc glycinate, both in the anhydrous form and in the monohydrate form has been found to be a highly effective deodorant in both preventing new odors and neutralizing existing odors, by chemical interaction with the odoriferous components. In addition, the zinc glycinate has been found to inhibit bacterial growth which further enhances its deodorancy properties by preventing bacteria to multiply and produce additional odoriferous components.

Although the present invention has been described and illustrated with reference to specific examples, it is understood that modifications and variations of composition and procedure are contemplated within the scope of the following claims.

I claim:

1. A method of deodorizing odorous body locations comprising contacting said locations with a deodorant composition comprising an effective deodorizing amount of a particulate zinc glycinate compound having a pH of about 7.9–8.7, which deodorizes within the pH range of about 8 and 7 by means of chemically neutralizing body odors by chemical interaction with the odoriferous compounds in sweat, and inhibits bacterial growth on the skin; dissolved and/or suspended in a cosmetically acceptable vehicle free of inorganic and organic acids and water soluble metal salts of fatty acids.

2. The method according to claim 1, wherein the deodorant active material is anhydrous zinc glycinate.

3. The method according to claim 1, wherein the deodorant active material is the hydrated form of zinc glycinate.

4. The method according to claim 1, wherein the deodorant active material constitutes about 1–50% by weight of the composition.

5. The method according to claim 1, wherein the vehicle is in the form of a lotion comprising a liquid carrier of a lower alcohol or an aqueous alcoholic media.

6. The method according to claim 4, wherein the composition contains a suspending or thickening agent and is dispensed from a roll-on container.

7. The method according to claim 5, wherein the lotion contains non-volatile polar or non-polar ingredients selected from the group consisting of polyhydric alcohols and emollient oils.

8. The method according to claim 1, wherein the vehicle is in the form of a stick comprising a monohydric or polyhydric alcohol gelled with a fatty alcohol or fatty amide or combination thereof.

9. The method according to claim 1, wherein the vehicle is in the form of a cream comprising an aqueous emulsion of a fatty material.

10. The method according to claim 1, wherein the zinc glycinate is suspended in a liquid vehicle comprising a carrier liquid and a liquified gaseous propellant, in the form of a deodorant spray.

* * * * *